United States Patent [19]
Webster et al.

[11] 4,037,970
[45] July 26, 1977

[54] OPTICAL ANALYZER FOR AGRICULTURAL PRODUCTS

[75] Inventors: Donald R. Webster, Laurel, Md.; Eugene R. Ganssle, Skillman, N.J.

[73] Assignee: Neotec Corporation, Silver Spring, Md.

[21] Appl. No.: 653,848

[22] Filed: Jan. 30, 1976

Related U.S. Application Data

[62] Division of Ser. No. 283,270, Aug. 24, 1972, abandoned, and Ser. No. 497,727, Aug. 15, 1974, and Ser. No. 420,863, Dec. 3, 1973, Pat. No. 3,861,788.

[51] Int. Cl.² .............................................. G01J 3/48
[52] U.S. Cl. .................................... 356/188; 350/266; 350/315; 350/318; 356/210
[58] Field of Search .................. 356/36, 39, 51, 83, 356/84, 96, 97, 99, 100, 179, 180–186, 188, 189, 195, 201, 204–206, 209–212, 243–246; 350/166, 266, 275, 311, 315, 318; 235/151.35; 250/226, 233

[56] References Cited

U.S. PATENT DOCUMENTS

| | | | |
|---|---|---|---|
| 2,406,318 | 8/1946 | Brace ........................... | 350/315 |
| 2,427,790 | 9/1947 | Korman ........................ | 356/185 |
| 2,670,400 | 2/1954 | Grunwald ..................... | 350/315 X |
| 2,852,693 | 9/1958 | Hughes et al. ................ | 250/71 |
| 2,960,909 | 11/1960 | Shipley ......................... | 356/30 |
| 2,984,146 | 5/1961 | Kwart et al. ................. | 356/51 |
| 3,205,355 | 9/1965 | Ehlert ........................... | 356/243 |
| 3,457,002 | 7/1969 | Magrath ....................... | 350/166 |
| 3,492,478 | 1/1970 | Smith ........................... | 350/315 X |
| 3,776,642 | 12/1973 | Anson et al. ................. | 356/188 |
| 3,828,173 | 8/1974 | Knepler ........................ | 356/188 X |

FOREIGN PATENT DOCUMENTS 896,736  5/1962  United Kingdom ............... 356/205

OTHER PUBLICATIONS

Hunter, Journal of the Optical Society of America, vol. 51, No. 5, pp. 552–554, May 1961.
Dickey-John brochure distributed at news conference on Aug. 5, 1971 in Illinois.
Neotec brochure distributed at news conference on Aug. 5, 1971 in Illinois.

*Primary Examiner*—F. L. Evans
*Attorney, Agent, or Firm*—Lane, Aitken, Dunner & Ziems

[57] ABSTRACT

An automatic test instrument for gaging the percentage of various constituents in organic substances by comparing the reflective optical density of the subject at various wavelengths. Narrow band optical filters are connected together in the form of a rotatable paddle wheel positioned so that the filters can be individually swept through the incident light path between the specimen and wideband light source. As the filter wheel turns, the band of light passed by each filter is progressively shifted with the changing angle of the filter relative to the light path. The filter wheel configuration includes opaque vanes extending from the ends of the filters to periodically interrupt the passage of light to the specimen. Photocells are positioned to sense the level of light reflected from the specimen. The output of the photocells is sampled at predetermined times relative to the rotation of the filter wheel to yield values indicative of reflected intensity at certain wavelengths. Using these values, an electronic circuit in one embodiment calculates three optical density difference values corresponding to moisture, protein and oil content of the specimen. The difference values are automatically inserted in three linear equations which are solved to obtain readings representing the true percentages of oil, water and protein contained in the specimen. Each time a new specimen is loaded for testing, the instrument is automatically calibrated against a standard sample, preferably Teflon (Trademark). The output of the photocells is amplified in a special circuit which subtracts the level of dark period current from the output when the photocells are illuminated.

16 Claims, 7 Drawing Figures

OPTICAL ANALYZER FOR AGRICULTURAL PRODUCTS

CROSS REFERENCE TO RELATED APPLICATIONS

This application is a divisional of application Serial No. 283,270 filed August 24, 1972, now abandoned, of application Serial No. 497,727 filed August 15, 1974 and application Serial No. 420,863 filed December 3, 1973, now Patent No. 3,861,788.

BACKGROUND OF THE INVENTION

The invention relates generally to the field of instruments for measuring and analyzing the optical properties of organic materials and, more particularly, to improved systems for measuring and analyzing optical densities of organic materials at various wavelengths to determine the percentages of certain constituents of the test material.

During the past few years there has been a growing need in the agricultural community for a versatile test instrument capable of rapidly determining moisture, oil and protein content in produce and grain products. The traditional analitical laboratory techniques, for example the Kjeldahl technique for measuring protein, are extremely accurate but require the use of skilled chemists, and the results are not readily available. Buyers of agricultural products have manifested increasing interest in obtaining data on the percentage of moisture, protein and oil contained in various products. In fact, the export market, particularly in wheat, has seen the widespread introduction of selling on the basis of guaranteed protein content. This competitive pressure increases the requirement for the commodity handler, from the country elevator to the export terminal, to be able to rapidly and accurately sort grains and other products by their protein percentage and oil and water content, where applicable. Specifically, the need is for a versatile, yet low cost piece of advanced equipment which combines and improves upon recent scientific findings in the field of non-destructive testing of agricultural products. For maximum usefulness of commodity handlers, the instrument must not place high demands on the skillfulness of the operator or require a specialized knowledge of the scientific basis for an end result.

Prior researchers have confirmed that non-destructive light transmittance and reflectance tests on various agricultural products can be indicative of their moisture content and other characteristics. It has been demonstrated that the amount of light reflected at certain wavelengths from a uniform specimen of grain, for example, is indicative of moisture, protein and oil content. A most valuable measurement in this regard has been found to be the difference in optical density, delta OD, at two characteristic wavelengths. Optical density, OD, refers to the ease with which light is transmitted through or reflected by an object. Reflective optical density, OD, is defined herein by the equation, $OD = \text{Log } 1/R$, where R, reflectivity, equals the ratio of the intensity of reflected light to the intensity of incident light at a particular wavelength, $(I_r/I_i)$. Thus, delta OD $= \text{Log } (I_i/I_r)_1 - \text{Log } (I_i/I_r)_2$, where the subscripts 1 and 2 indicate the two different wavelengths used for the measurement of delta OD. If the intensity of incident light at both wavelengths is approximately the same, then delta OD $= \text{Log } (I_r)_2 - \text{Log } (I_r)_1$. Thus, it is known that by subtracting the two logarythms of the intensity of reflected light, an indication of the difference in reflective optical density can be obtained.

Research by the U.S. Department of Agriculture and other governmental agencies has indicated that individual $\Delta OD$ readings selected to measure water, oil and protein content are interrelated. The following three equations have emerged from these studies as reliable indicators of the percentage of these constituents in agricultural products:

$$\text{oil \%} = K_0 + K_1 (\Delta OD)_w + K_2 (\Delta OD)_o + K_3 (\Delta OD)_p, \tag{1}$$

$$\text{water \%} = K_4 + K_5 (\Delta OD)_w + K_6 (\Delta OD)_o + K_7 (\Delta OD)_p, \tag{2}$$

$$\text{protein \%} = K_8 + K_9 (\Delta OD)_w + K_{10} (\Delta OD)_o + K_{11} (\Delta OD)_p, \tag{3}$$

where $K_0$ to $K_{11}$ are constant coefficients or "influence factors" and the subscripts $w$, $o$ and $p$ indicate that the wavelengths at which the associated $\Delta OD$ measurements are made are selected for their sensitivity to water, oil and protein content respectively. Before calculating the percentage constituents from the above equations, three different $\Delta OD$ measurements must be performed on the specimen. Each $\Delta OD$ requires measurements at two different wavelengths. Accordingly, six different wavelengths must be available. An instrument with the versatility to perform measurements on different agricultural products must be capable of switching from one set of six wavelengths to another set characterizing the optical properties of the product being tested.

Prior art devices for measuring $\Delta OD$ employed a plurality of filters passing discrete nonvariable wavelengths. In the copending application Ser. No. 234,843, now U.S. Pat. No. 3,765,775 a specimen is illuminated with light sequentially filtered by a continuously rotating disc carrying a plurality of narrow band optical interference filters. The combined output of several photocells positioned to receive light reflected from the specimen is selectively sampled after passing through a logarithmic amplifier to obtain $\Delta$ OD measurements. $\Delta$ OD readings at two discrete wavelengths are compared in a differential amplifier to provide a $\Delta$ OD measurement. Although this system is satisfactory for its intended purpose, the ability to make readings at various wavelengths is naturally limited by the number of filters carried by the disc. Without substituting a different filter, it is not possible to take readings at wavelengths between those of two filters having adjacent wavelengths.

A new optical filtering approach has recently been studied at the U.S.D.A. Agricultural Research Service in Greenbelt, Maryland. An ordinary narrow band with optical filter arrangement includes a planar interference filter inserted perpendicularly to the optical path between a wideband light source and the specimen. It has been found that by tilting the filter several degrees off the perpendicular orientation, the bandwidth may be shifted substantially, due to the difference in the apparent thickness of the filter as "seen" by the light source when the filter is tilted. If the filter is mounted for rotation through the optical path, the output of the filter is a continuously changing characteristic frequency over a limited range.

This system has been applied to Δ OD measurements of agricultural products. Each pair of discrete filters for a given Δ OD measurement, may be replaced by a single tilting filter, provided that the two frequencies of interest are close enough together. Of course, one of the essential advantages is that any frequency in the range "swept" by the tilting filter can be selected as desired, so that various OD meansurements may be carried out on different specimens without changing the filter. One of the problems solved by the invention is incorporating the tilting filter technique in a fully automatic test instrument for use by unskilled operators.

A related problem arises in amplifying the output of the photocells. Because of the extreme sensitivity of photocells in current use, such as the lead sulphide type, the response of the photocell to light must be regularly compared or referenced to its response to darkness. In the past, rotating partial discs, called light choppers, have been used to provide alternating periods of darkness and illumination. The photcell's alternating output was capacitively coupled to a high gain amplifier and later demodulated to provide a DC (direct current) level representing the difference between the light and dark output. Besides requiring a very high voltage DC source before the amplifier, the demodulating technique superimposed noise on the photocell signal.

SUMMARY OF THE INVENTION

Accordingly, the general purpose of the invention is to provide rapid computations of the percentages of certain constituents based on measurements of reflective optical density of various organic materials at certain wavelengths of light. One of the more specific objects of the invention is to utilize the tilting filter technique in a more efficient manner to pass light of continuously changing wavelength in the ranges associated with each one of a plurality of filters. An objective of the filter design is to incorporate means for blocking the passage of light at regular intervals to provide dark periods. Another object of the invention is to systematically sample the invensity of light reflected from the specimen and to compare and store light levels at various wavelengths in order to calculate the moisture, protein and oil content of the specimen with predetermined formulas or equations.

These and other objects of the invention are achieved by a fully automatic, table-top instrument which directly displays the moisture, protein and oil content of organic materials, based on the principle that certain wavelengths of light are absorbed in relation to the concentrations of these constituents in the material tested. Three Δ OD values are automatically generated in accordance with the characteristics of the reflection spectra attributable respectively to the moisture, protein and oil content of the test specimen. Analog computing circuits solve the percentage equations (1), (2) and (3), above, based on the Δ OD measurements and predetermined constants.

A source of wideband infrared light illuminates a slidable sample drawer carrying both a standard or reference sample and a uniform specimen of the product under test. A multiple filter assembly in the form of a paddlewheel is mounted for rotation about an axis perpendicular to and spaced from the light path between the drawer and the light source. Each filter is a planar, narrow bandwidth optical interference plate having one edge connected along its length to a common axle. The preferred embodiment has three filters which pass different characteristic frequencies. A cross-section of the paddlewheel assembly thus resembles a letter "Y" with the filters extending radially from the axle in different planes which all intersect in a line approximately coincident with the axis of rotation. The filters are equally separated angularly by about 120°. As each filter sweeps through the light path, the narrow bandwidth output of the filter is shifted continuously as a function of the angle between the plane of the filter and the light path. In the preferred embodiment, the frequencies swept by the tilting filters are in three adjacent, successively higher bands of infrared light providing in combination a wide range of frequencies of interest. An opaque vane is connected perpendicularly to the end of each filter. The vanes pass into the light path and periodically interrupt illumination of the sample drawer to provide regular dark periods.

A plurality of photo-sensitive elements or photocells are located just above the drawer out of the incident light path to sense the intensity of light reflected from the specimen. The combined output of the cells is fed to a sensor amplifier unit which automatically corrects the illuminated output by regularly subtracting a stored DC dark period level from the illuminated level. The output of the sensor amplifier unit is passed via a logarythmic amplifier to a pair of sample and hold circuits individually gated by a logic unit responsive to the instantaneous orientation of the filter assembly. Each sample and hold circuit samples the output of the logarythmic amplifier at times corresponding to different wavelengths passed by one of the filters. The sample and hold circuit outputs are connected to opposite inputs of a differential amplifier whose output is connected to several additional sample and hold circuits. One of the latter sample and hold circuits is gated by the logic unit after the second sample is obtained during the passage of each one of the filters. After one complete revolution of the paddlewheel in the preferred embodiment, the latter sample and hold circuits store signal levels representing the Δ OD values corresponding to moisture, oil and water content, respectively.

The outputs of the latter sample and hold circuits are connected via respective calibration units to a computing and display unit containing analog computing circuits which, in the preferred embodiment, solve the percentage equations (1), (2) and (3), above, based on the stored Δ OD values and predetermined constants. The percentages of moisture, protein or oil in the specimen are displayed digitally.

The calibration units serve to adjust each Δ OD value in accordance with the outputs of the photocells when the standard sample is illuminated. When the drawer is pulled out to provide access to the test specimen, the sample is automatically positioned in the light path, and a switch is automatically thrown which blanks the display and causes the computed Δ OD values for the standard to be stored. When the drawer is slid back to place the specimen in the light path, the Δ OD values for the standard are subtracted from the respective Δ OD values generated for the specimen. In practice, the compound polytetrafluoroethylene, PTFE (sold under the trademark "Teflon" by Dupont, Inc.), is used for the standard sample because its optical qualities closely parallel those of many grain products.

In the preferred embodiment the logic unit products 1000 counts per paddlewheel revolution representing increments in angular position. 100 counts are alloted to each filter as it passes through the light path. The first two sample and hold circuits may be connected to respond to any two positions of each filter among the 100 positions.

Different kinds of agricultural products have different characteristic frequencies indicative of moisture, protein, oil and other constituents. The instrument can accommodate various products by sampling different frequencies without physically changing the optical filters. As agricultural research uncovers new test wavelengths more indicative of moisture content, for example, for indicative of different important constituents, the instrument can be easily adapted to accommodate these new findings.

DESCRIPTION OF THE PREFERRED EMBODIMENTS

Figure 1:
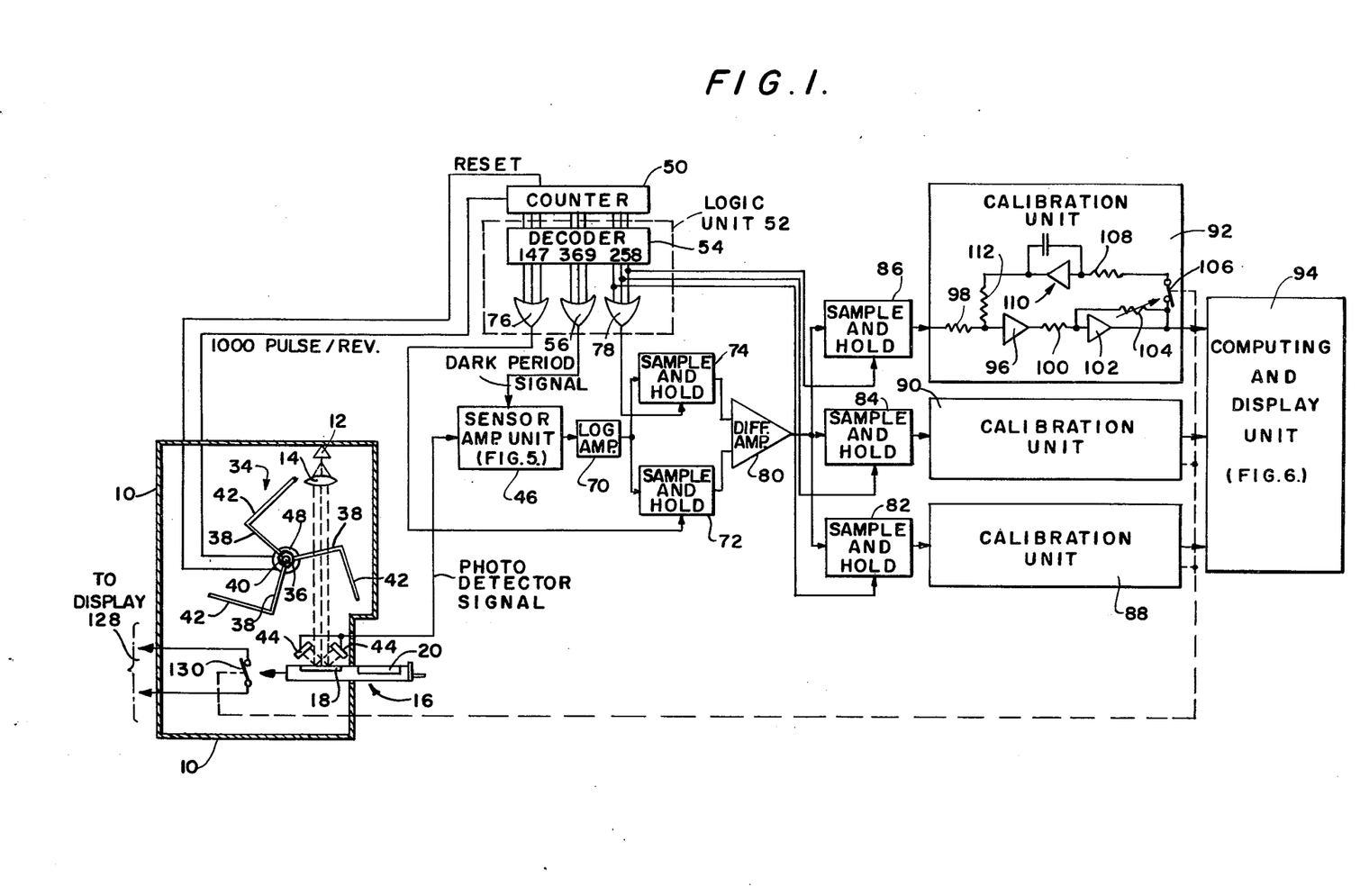
FIG. 1 is a schematic and block diagram illustrating an embodiment of the invention.

In FIG. 1 an example of the complete test instrument is shown is schematic form. In practice the optomechanical sensing components of the system are mounted in a housing 10 with the electronic computing elements in a separate module (not shown). Light from a high intensity wide band infrared lamp 12 is directed through a collimating lens 14 to illuminate an area on a sample drawer 16. The drawer 16 is slideably mounted through an opening in the wall of the housing 10 so that it can be moved between two positions. The drawer 16 is adapted to carry two samples. A standard sample 18 used in calibrating the test equipment is mounted on the interior upper surface of the sample drawer 16. A uniform test sample 20 of an agricultural product, such as soybeans, wheat, corn or mylo, is placed at the other end of the upper surface of the sample drawer 16. When the drawer 16 is pulled approximately half-way out of the housing wall, the test sample 20 is exposed for inspection or reloading, and the standard sample 18 is positioned in the area illuminated by the lamp 12, as shown in FIG. 1. When the sample drawer 16 is pushed into the housing 10 )to the left as viewed in FIG.1) the test sample 20 is illuminated and the standard sample 18 is removed from the light path. By this arrangement, one simple movement of the drawer 16 correctly positions the standard sample 18 and allows access to the test sample 20.

In practice, a suitable material for the standard sample 18 has been found to be polytetrafluoroethylene, PTFE (sold under the trademark "Teflon" by Dupont, Inc.). Other standards may be used, but PTFE is preferred because its optical properties match those of many grains.

The test sample portion of the drawer 16 may simply comprise a well into which a ground sample of a substance like wheat may be poured and then leveled off flush with the top of the drawer. Instead of pouring the prepared sample directly into the sample drawer 16, the removable sample holder or cartridge 22, shown in FIG. 2, may be employed. The puck-shaped cartridge 22 comprises an externally threaded, ring-shaped member 24 having a disc-shaped transparent glass window 26 spanning one side. A disc-shaped compressor plate 28 is fitted loosely into the open side of the ring-shaped member 24. The compressor plate 28 carries springs 30 or other suitable resilient material on its outer side. An internally threaded retainer cap 32 is received on the ring-shaped member 24. The cap 32 presses against the springs 30 urging the compressor plate into the ring-shaped member 24.

Figure 2:
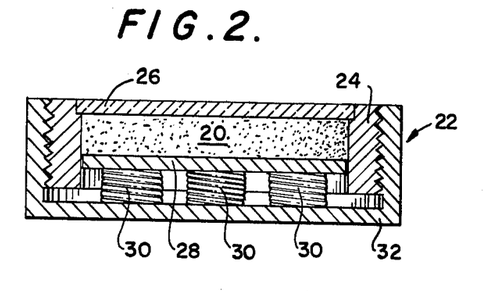
FIG. 2 is a sectional view of a sample holder used in the apparatus of FIG. 1.

When loading the cartridge 22, the cap 32 and the compressor plate 28 are removed from the ring-shaped member 24, which is inverted and loaded with the prepared sample material 20. The compressor plate 22 is then inserted, and the cap 32 is screwed on compressing the sample material 20 between the glass window 26 and the compressor plate 28. The entire cartridge 22 is then placed into a suitable well formed in the sample drawer at the position of the sample 20, shown in FIG. 1, with the glass window 26 facing towards the lamp 12.

Figure 3:
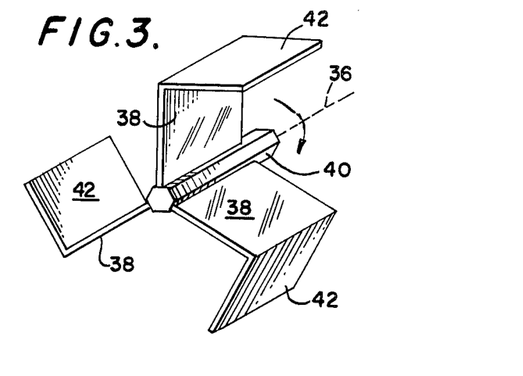
FIG. 3 is a schematic diagram illustrating the paddlewheel of FIG. 1 in an isometric view.

A multiple filter assembly 34 (FIGS. 1 and 3) in the form of a paddlewheel is mounted for rotation about an axis 36 perpendicular to and spaced from the light path defined between the lamp 12 and the illuminated area on the sample drawer 16. In the preferred embodiment, three narrow band width plate-shaped optical interference filters 38 are mounted on an axle 40 having a hexagonal cross-section. The respective planes of the filters 38 are equally separated angularly by about 120°. The filters extend radially from the axle in different planes which all intersect in a line approximately conincident with the axis of rotation 36. The filters 38 extend equal radial distances from the axle 40. The configuration of the filters 38 on the axle 40 resembles the letter "Y" in cross-section as viewed in FIG. 1. An opaque vane 42 is attached perpendicularly to the outer end of each filter 38. The axis of rotation 36 is spaced laterally from the light path between the lamp 12 and the drawer 16 so that the filters 38 swing through the light path one-at-a-time. Between successive sweeps of adjacent filters 38, an opaque vane 42 swings through the light path interrupting illumination. As each filter 38 swings through the light path, the angle between the plane of the filter 38 and the light path changes continuously. Because of this changing angle, the band of light transmitted by the filter 38 is continuously shifted due to the change in apparent thickness of the filter 38 as "seen" by the lamp 12.

Figure 4:
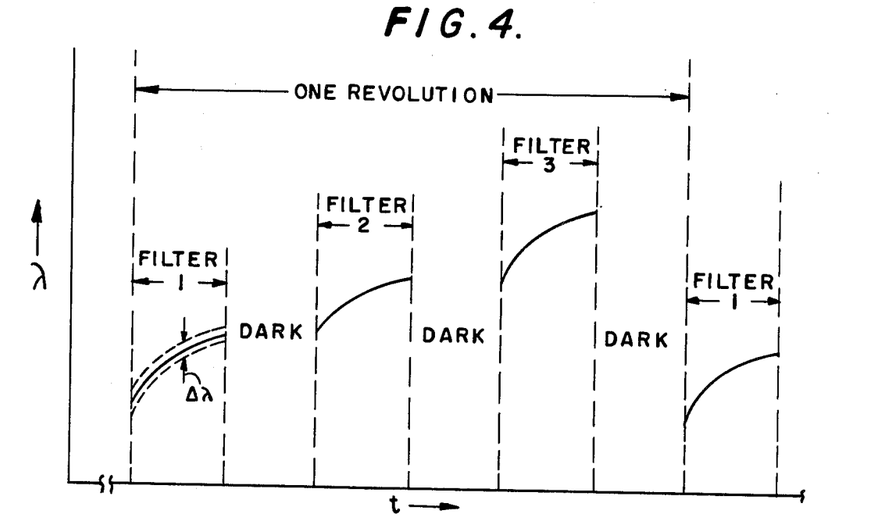
FIG. 4 is a graph representing the wavelengths of light passed by the paddlewheel of FIG. 1 during rotation.

The sequential illumination of the sample drawer 16 is represented by the graph in FIG. 4, wherein the vertical axis represents increasing wavelength and the horizontal axis represents time. During the period in which the first filter is in view, that is, intercepting the light from the lamp 12, the central wavelength of light passed to the sample drawer 16 increases progressively. The solid, dark, curved line in the first filter period in the graph of FIG. 4 is intended to represent the central wavelength within a narrow band of wavelengths $\Delta\lambda$, passed by the filter 38. The output of the first filter represented corresponds to positions of the filter as the paddlewheel rotates clockwise from the point where the filter first enters and complete intercepts the light path to a point at which the filter is approximately perpendicular to the light path. As the filter rotates further below the perpendicular orientation, the same band of wavelengths would be passed redundantly; however, this subcycle of operation is interrupted by the vane 42 attached to the adjacent filter 38. During interruption of illumination by the vane 42, a dark period is provided as indicated in FIG. 4. Following the dark period, the next filter is swung through the light path sweeping another band of wavelengths. The optical properties of the filter 38 are selected so that frequency bands of interest are passed during one revolution of the paddlewheel. In the preferred embodiment of the characteristic pass bands of the filters (that is the central wavelengths passed when the filter is in the perpendicular or normal orientation) are chosen so that the filters will sweep out contiguous frequency bands spanning almost the entire near infrared band from about 1800 nm (nanometers to about 2320 nm. This band includes wavelengths of interest in testing grain and grain products.

Figure 5:
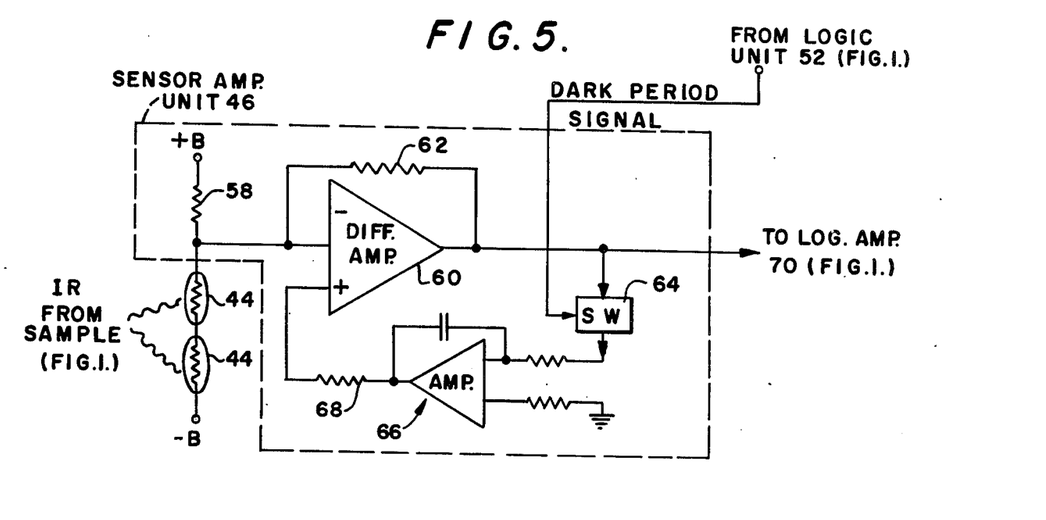
FIG. 5 in a schematic and block diagram illustrating the sensor amplifier unit of FIG. 1 in more detail.

A pair of electrically interconnected photocells 44 are mounted in the housing 10 (FIG. 1) immediately above the sample drawer 16 on opposite sides of the light path to receive light reflected from the sample 18 or 20. The combined output of the photocells 44 is passed to a sensor amplifier unit 46 (FIGS. 1 and 5). The amplifier unit 46 has two functions: (1) to amplify the signal, and (2) to correct the output of the photocells 44 in accordance with their response during the dark periods.

A pulse-type angle transducer 48 (FIG. 1), responsive to rotation of the paddlewheel axle 40, produces an electrical output indicative of the instantaneous orientation of the paddlewheel 34. The transducer 48 produces two separate outputs to a counter 50 (FIG. 1). One of the transducer outputs provides 1000 pulses per revolution of the paddlewheel 34 and is connected to the load input of the counter 50. The other output of the transducer 48 provides one reset pulse for the counter 50 per revolution of the paddlewheel. Accordingly, during one revolution of the paddlewheel, the counter 50 counts up to 1000 and is then reset to zero for the next revolution during which 1000 counts are again recorded.

The counter 50 produces parallel outputs to a logic unit 52. The purpose of the logic unit 52 is to provide individual output signals corresponding to preselected positions or orientations of the paddlewheel 34, indicative of the wavelength of light falling on the sample drawer 16. The logic unit 52 includes a decoder 54 which receives the parallel outputs of the counter 50 and provides pre-programmed output signals indicative of various paddlewheel orientations. One set of three outputs from the decoder 54 is passed via an OR gate 56 to the sensor amplifying unit 46 in order to identify the three dark periods during which the opaque vanes 42 intercept the light from the lamp 12. Each one of the three outputs from the decoder 54 to the OR gate 56 represents a 100 count period during which a corresponding vane 42 swings through the light path. Accordingly, the dark period signal issuing from the OR gate 56 to the amplifier unit 46 occurs for three 100 count intervals during each revolution of the paddlewheel 34.

The sensor amplifier unit 46 shown in FIG. 5 represents an embodiment adapted for use with a pair of series-connected photo-resistive-type photocells 44. The two photocells 44 are connected in series to one end of a fixed resistor 58. The other end of the resistor 58 is connected to a source of positive DC voltage on the order of +15 volts. The photocells 44 are connected to a source of negative DC voltage on the order of −15 volts. The junction between the resistor 58 and the adjacent photocells 44 is directly connected (DC coupled) to the positive input of a differential amplifier 60 having a feedback resistor 62 connected between the output and the positive input. The output of the differential amplifier 60 is connected via a switch 64 operated by the dark period signal from the logic unit 52 (FIG. 1) to an integrating amplifier circuit 66. The output of the integrating amplifier circuit 66 is connected via a series resistor 68 to the negative input of the differential amplifier 60. The output of the sensor amplifier unit 46 is the output of the differential amplifier 60.

During a dark period provided by one of the paddlewheel vanes 42 (FIG. 1), the switch 64 is closed causing the output of the differential amplifier 60 to go to zero. The output of the integrating amplifier 66 registers the dark period level. When the next filter comes into position, the input to the integrating amplifier 66 is disconnected by the switch 64 in response to the removal of the dark period signal. At the same time, however, the stored output of the integrating amplifier 66 is substracted in the differential amplifier 60 from the signal produced by the photocell circuit. Accordingly, the output of the sensor amplifier unit 46 takes into account the changing dark period response of the photocells 44 by adjusting the amplifier output during the periods of illumination. In contrast, in prior art sensor amplifiers used in other types of optical equipment, the photocell signal is capacitively coupled to an amplifier and later demodulated to provide a DC output indicative of the difference between alternating high and low (dark) levels. This required an application of high voltage to the photocell, on the order to 500 volts and the demodular superimposed noise on the signal.

In FIG. 1 the output of the sensor amplifier unit 46 is passed via a logarithmic amplifier 70 to the inputs of a pair of sample and hold circuits 72 and 74. The control inputs or sample gages for the circuits 72 and 74 issue from the logic unit 52 at times corresponding to the occurrence of successive discrete wavelengths of interest. Within the logic unit 52, three outputs of the decoder 54 are passed via an OR gate 76 to control the sample and hold circuit 72, another set of three outputs from the decoder 54 is passed via another OR gate 78 to control the sample and hold circuit 74. The order of occurrence of the decoder outputs, including dark periods and discrete wavelengths signals, is indicated by the numbers within the decoder block in FIG. 1. In the preferred mode of operation, the sample and hold circuits 72 and 74 are each gated on once at different times during a sweep of each filter 38 through the light path. Thus, while one filter 38 is sweeping through the light path, the sample and hold circuit 72 will be activated at a first predetermined time corresponding to a certain wavelength, followed by activation of the sample and hold circuit 74 at a second predetermined time corresponding to another particular wavelength. Next, one of the vanes 42 causes a dark period signal followed by entry of the next filter 38 into the light path, whereupon the sample and hold circuits 72 and 74 are again activated in succession. All the sample and hold circuits in the electronic circuitry are conventional in design and rapidly sample the signal level and store a voltage representing that level until a subsequent control signal is applied.

The respective outputs of the sample and hold circuits 72 and 74 are fed to opposite inputs of a differential amplifier 80 which produces an output representing the difference between the values stored in each sample and hold circuit 72 and 74 at any given time. The difference output may be represented as before by the expression $\log (I_r)_1 - \log (I_r)_2$ which is directly proportional to $\Delta$OD. $(I_r)_1$ and $(I_r)_2$ are the measured reflected intensities at the pair of sampled wavelengths. The output of the differential amplifier is connected to the inputs of three additional sample and hold circuits 82, 84 and 86. The circuits 82 84 and 86 are controlled by the logic unit 52 and are connected respectively to the outputs of the decoder 54 which are passed to the OR gate 78. Accordingly, the output of the differential amplifier 80 is sampled and stored in the circuit 82 following the taking of the two samples stored in the hold circuits 72 and 74. During the passage of the next filter 39, the next sample and hold circuit 84 is activated after the second sample is stored by the circuit 74. A third $\Delta$OD value is similarly stored in the sample and hold circuit 86 during the third filter period. While the control input for the circuits 82, 84 and 86 are shown symbolically as identical to the decoder outputs passed to the OR gate 78 for operation of the sample and hold circuit 74, in reality a few counts delay should be allowed between activation of the circuit 74 and eachone of the circuits 82, 84 and 86 to allow the $\Delta$OD value to be generated before sampling the differential amplifier output.

Following one complete revolution the sample and hold circuits 82, 84 and 86 each store signal levels representing three respective $\Delta$OD measurements at three respective pairs of wavelengths selected by the decoder 50. While the wavelength pairs selected in the preferred embodiment correspond to three different filters respectively, it is possible to select wavelengths in any order without regard to the order of the filter sweeps by means of appropriate programming of the decoder 54.

The outputs of the sample and hold circuits 82, 84 and 86 are passed via respective calibration units 88, 90 and 92 to a computing and display unit 94. Because of the possibility of voltage drift or other irregularities in the analog electronic equipment utilized in the system, it is advantageous to re-establish a correlation between the output of the instrument and a reference or standard sample from time to time. An extremely convenient and fool-proof technique for calibrating the output of the sample and hold circuits of 82, 84 and 86 is shown in FIG. 1. The contents of calibration unit 92 are shown in detail in FIG. 1 and the contents of the other calibration units 88 and 90 are identical, although capable of independent adjustment as will be discussed.

The calibration unit 92 contains a first amplifier 96 which receives as an input voltage the signal level stored in the sample and hold circuit 86 via a limiting resistor 98. The output of amplifier 96 is passed via a resistor 100 to a second amplifier 102 having a manually adjustable feedback resistor 104. The output of the amplifier 102 forms the output of the calibration unit 92 to the computing and display unit 94. The output of the amplifier 102 is also fed back via a switch 106 and a series resistor 108 to an integrating amplifier 110, whose output is fed via a series resistor 112 to the input of the amplifier 96.

The switch 106 in the calibration unit 92 (and similar switches in units 88 and 90) is operated by the movement of the sample drawer 16. As shown in FIG. 1, the switch 106 is in its closed position when the sample drawer 16 is pulled out to position the standard sample 18 in the light path. The signal level stored in the sample and hold circuit 86 while the standard sample 18 is illuminated via the rotating paddlewheel 34 is amplified and inverted by the amplifier 96. The original polarity of the output of the sample and hold circuit 86 is restored by the amplifier 102. The output of the amplifier 102 is stored in the integrating amplifier 110 while the switch 106 is closed with the standard sample in position. When the sample drawer 16 is pushed back into its test position at which the prepared sample 20 is in the light path, the switch 106 of the calibration unit 92 is opened breaking the connection between the integrating amplifier 110 and the amplifier 102. The output of the integrating amplifier 110 is inverted with respect to the input of the amplifier 96 from the sample and hold unit 86. Accordingly, the value stored in the integrating amplifier 110 is substracted continuously from the input to the amplifier 96 from the circuit 86, thus, the $\Delta$OD value stored in the sample and hold circuit 86 is continuously referenced against the $\Delta$OD generated when the standard sample 18 is in position. The standard sample 18 is a material, preferably PTFE, which approximates the reflective characteristics of the sample being tested.

The calibration units 88and 90 receiving the outputs of the sample and hold circuits 82 and 84, respectively, operate in a similar manner when the sample drawer 16 is pulled out. All of the switches 106 in the calibration unit 92 are ganged together and are operated simultaneously when the drawer 16 is moved in or out.

Figure 6:
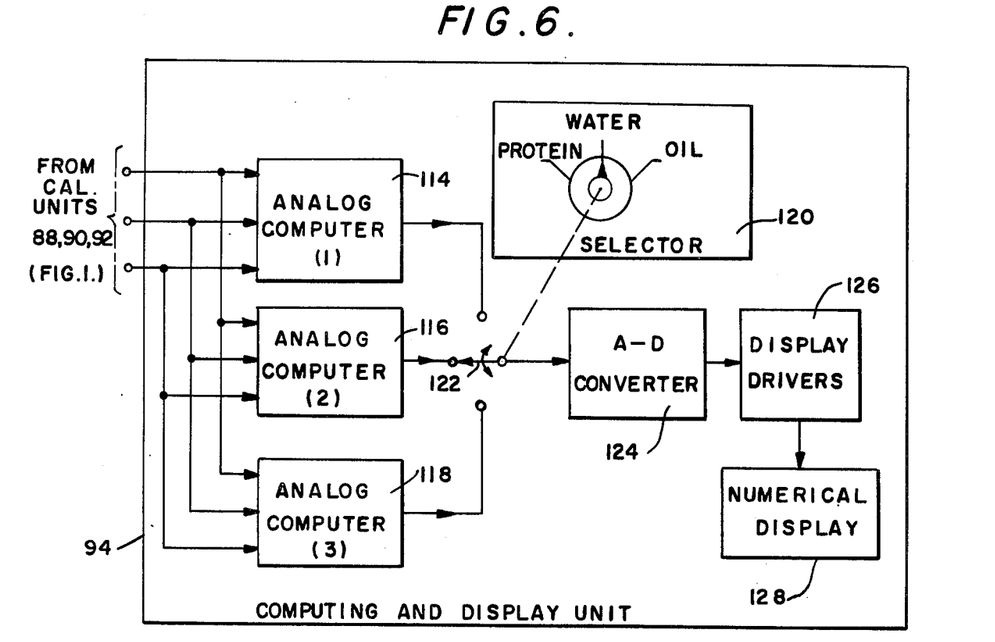
FIG. 6 is a schematic and block diagram illustrating the computing and display unit of FIG. 1 in more detail.

The outputs of the calibration units 88, 90 and 92 are passed to a computing and display unit 94, as shown in FIG. 6, containing three analog computer circuits 114, 116 and 118. Each computer circuit contains standard pre-programmed analog circuitry for calculating the percentage of the corresponding constituent based on the corresponding equation from the set (1), (2) and (3), above. Each computer 114, 116 and 118 receives all three $\Delta$OD outputs from the calibration units 88, 90 and 92 simultaneously. Within the computer circuit 114, for example, each $\Delta$OD value is multiplied by a predetermined constant ($K_1$, $K_2$, $K_3$ and then the products are summed with a forth constant ($K_0$). The resulting output of the computer 114 is indicative of the percentage of oil contained in the test sample. The operation of the computer circuits 116 and 118 are similar and the resulting outputs indicate the percentages of protein and water respectively. An output selector 120 operates a switch 122 which selectively connects one of the outputs of the computer circuits 114, 116 and 118 to an analog-to-digital converter 124. The output of the converter 124 is passed via display drivers 126 to a numerical display 128 for example, containing a plurality of Nixie (Trademark) tube digits. When the sample drawer is pulled out positioning the standard 18, another switch 130 ganged with the switches in the calibration units 88, 90 and 92 is thrown. The switch 130 is connected to blank the display 128 when the standard sample 18 is in the light path.

Additional coefficients are introduced in equations (1), (2) and (3), above, by the adjustable resistor 104 in the calibration unit 92 and similar resistors in units 88 and 90. These resistors serve to change the gain or multiplier factors applied to the $\Delta$OD values generated by the sample and hold circuits 82, 84 and 86 as amplified and corrected by the calibration 88, 90 and 92. If the additional coefficients are represented as $C_1$, $C_2$, and $C_3$ for the three calibration units, the resulting equations solved by the analog computers 114, 116 and 118 take the form:

$$\text{Oil\%} = K_0 + K_1 (C_1 \Delta OD_w) + K_2(C_2 \Delta OD_0) + K_3 (C_3 \Delta OD_p).$$

In this manner, the relative values or weights of the $\Delta OD$ measurements may be changed without altering the constants stored in the analog computers 114, 116 and 118. A change in these coefficients may be necessitated, for example, by extreme temperature changes in the filter assembly 34.

The constants ($K_0$ to $K_{11}$) in the equations (1), (2) and (3), above, vary depending on the type of agricultural product being tested. The appropriate values for the constants can be ascertaind by obtaining $\Delta OD$ readings for various samples of a certain type of grain or agricultural product and then subjecting the samples to the standard chemical or analytical test procedures to determine the percentage of moisture, protein and oil contained in the various samples. The three expressions for moisture, protein and oil are set equal to the analytical values and the resulting simultaneous linear equations are solved to arrive at the values of the constants.

Figure 7:
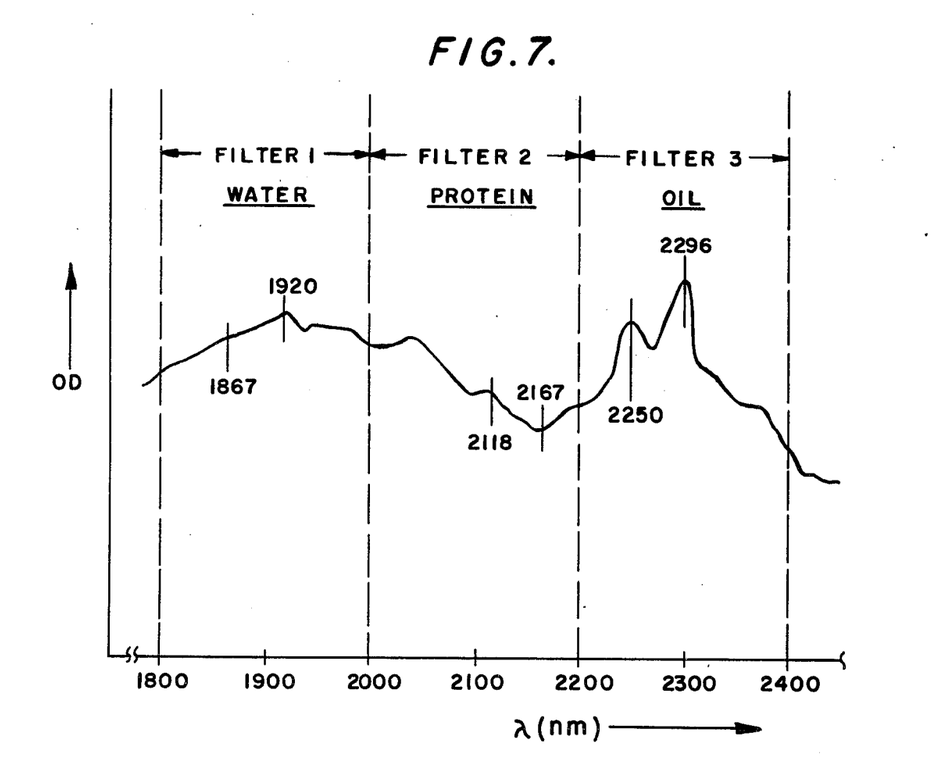
FIG. 7 is a graph representing the relationship between reflective optical density and wavelength in a typical grain sample.

The wavelengths at which $\Delta OD$ is measured depend on the type of product being tested. A graph of $OD$ versus wavelength (in nanometers) for a typical grain sample is shown in FIG. 7. The three pairs of wavelengths whose relative optical densities are significant indicators of water, protein and oil constituents, respectively, in the grain are indicated in the graph. For example, for calculating the $\Delta OD$ value corresponding to the contribution to the reflective spectra by the water content of the sample, the $\Delta OD$ at 1867mn and 1920 mn is calculated. These two wavelengths are sampled by the apparatus of FIG. 1 by programming the decoder 54 and the logic unit 52 so that the first two control signals passed to the sample and hold circuits 72 and 74 correspond to times during the rotation of the paddlewheel 334 at which these two wavelengths are passed by the first filter. The same technique is employed in selecting the times for gating the sample and hold circuits 72 and 74 when the other two filters swing through the light path.

Those skilled in the art will recognize that the equipment described herein is not necessarily restricted to any particular type of test sample; nor is it restricted to measurements of moisutre, protein and oil. The number of filters carried by the filter wheel 34 is not restricted to three: two filters, four filters or more may be spaced about the axle of the paddlewheel 34 to cover different bandwidths of light. If the wavelengths at which $\Delta OD$ is to be measured for a particular test product lie outside of the infrared region, different light sources can be substituted for the infrared lamp 12.

The three sample and hold circuits 82, 84 and 86 and their associated calibration units may be expanded to any number required for different calculations. For example, it may be found that a particular percentage measurement is only poorly approximated by a linear combination of three $\Delta OD$ values. It may, for example, take five $\Delta OD$ values in linear combination to obtain agreement with the true percentage as measured by chemical analysis. In this case, two more sample and hold circuits would be added to the existing circuits 82, 84 and 86 and the logic unit 52 would be implemented so that the system would provide five $\Delta$ OD readings per revolution of the paddlewheel 34. In addition, the analog computer circuitry as represented, for example, by computer 114 would have to be changed accordingly in an obvious manner.

It is expected that the operating principles described herein will find obvious application in many other types of equipment. In particular, the sensor amplifier unit 46 (FIG. 5) is applicable to other measuring systems using light sensors, such as spectrophotometers, thermal sensors, pollution sensors, as well as devices for measuring the absorption associated with certain constituents in grain products.

It is also noted that any of the analog components of the described system may be replaced by digital devices in an obvious manner.

The constants $K_0$ to $K_{11}$ in the equations (1), (2) and (3), above, can be established in the computers 114, 116 and 118 by any conventional programming means. Versatility is gained by using a set of insertable "Q" cards bearing the constants associated with different agricultural products and the six counts or "data points" designating the wavelengths at which the samples are to be taken. Thus, to change over from corn to wheat, the operator would just insert a different card. The instrument is operated by simply placing a prepared sample into the sample holder drawer, inserting the drawer and reading the display.

One of the most important features of the disclosed apparatus is its unprecedented speed in arriving at percentages with the same accuracy as lengthy laboratory procedures. In tests with an instrument constructed according to the invention, accuracy was within 0.10% for water and protein content in flour as compared to measurements by Kjeldahl analysis. Similar accuracy is attained for many other grains and grain products. Another advantage of the instrument is that its accuracy is "internal" and thus invulnerable to accidental or intentional tampering. If desired, the entire unit, except for the slidable sample drawer, can be sealed to assure tamperproof operation. The possibility of operator-error is eliminated by automatic self-calibration. It is impossible to measure a new sample without recalibrating the instrument because of the unique double sample drawer arrangement. The paddlewheel filter assembly employing the tilting filter technique eliminates the need for perfect manufacture of discrete filters. In addition, hundreds of wavelengths or data points are available. As research continues, new measurements can be made without any fundamental change in the deisgn. Packaging the opto-mechanical sensing unit separately from the computing units allows substitution of different electronic equipment without interfering with the sensing portion of the instrument.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim,

1. Optical apparatus, comprising a source of wide band light for illuminating an object, a multiple filter assembly having a rotatable axle and a plurality of narrow bandwidth optical interference filters fixed to said axle and radiating therefrom at the same axial location in respective planes forming therewith a paddlewheel configuration, said filter assembly being positioned relative to the light path defined between said light source and the object such that said filters are swept through said light path individually during rotation of said axle, said wide band light impinging on each successive one of said filters as the orientation thereof relative to said light path is changing, whereby light passing through each one of said filters is restricted to continuously shifting bandwidths as a function of the instantaneous angle between said light path and a given filter during rotation, photosensitive means positioned to receive light from said source of light after passing through one of said filters and coming into optical contact with said object and to produce a signal representative of the level of light received, and means responsive to said signal to provide an indication of a characteristic of said object.

2. The apparatus of claim 1, wherein said filters are equally spaced angularly about said axle, and the planes of said filters interesect approximately in a line coincident with the axis of rotation of said filter assembly.

3. The apparatus of claim 2, wherein the axis of rotation of said filter assembly is approximately perpendicular to and spaced laterally from said light path.

4. The apparatus of claim 3, wherein said filters are three in number.

5. The apparatus of claim 1, wherein the optical characteristics of said filters are predetermined such that the respective ranges of wavelengths passed by said filters during rotation are approximately contiguous, whereby a composite range of wavelengths is spanned during each complete revolution of said filter assembly.

6. The apparatus of claim 1, further comprising drive means operatively connected to said axle for imparting continuous rotation thereto, the position of said axle along the axis of rotation being fixed.

7. The apparatus of claim 1, further comprising means fixed to and extending from the outer end of at least one of said filters for at least partially interrupting the passage of light from said light source to the object.

8. The apparatus of claim 7, wherein said interrupting means includes a vane extending perpendicularly to the plane of the filter.

9. The apparatus of claim 1, further comprising a substantially opaque vane fixed to the outer end of each of said filter and extending perpendicularly to the plane of said filter a predetermined distance such that the passage of light from said source to the object is interrupted for a period of time between sweeps of adjacent filters through said light path.

10. The apparatus of claim 1, further comprising transducer means responsive to the rotation of said axle for providing a fixed number of pulses per axle revolution, counter means connected to receive the output of said transducer means for registering the number of pulses produced thereby per revolution, and logic means operatively connected to said counter means for providing a plurality of output signals at times corresponding approximately to predetermined discrete orientations of each said filter in said light path.

11. Optical apparatus, comprising a source of wide band light for illuminating an object, a multiple filter assembly having a rotatable axle and a plurality of narrow band width optical filters fixed to said axle and radiating therefrom at the same axial location in respective planes forming therewith a paddlewheel configuration, said filter assembly being positioned relative to the light path defined between said light source and the object such that said filters are swept through said light path individually during rotation of said axle such that light passing through each one of said filters is restricted to continuously shifting band widths corresponding to the instantaneous angle between said light path and a given filter during rotation, said filter assembly further including substantially opaque vanes each fixed to the outer end of a respective one of said filters and extending perpendicularly to the plane of said filter a predetermined distance such that the passage of light from said source to the object is interrupted for a period of time between sweeps of adjacent filters through said light path, at least one photosensitive means positioned to receive light from said source after passing through one of said filters and coming to optical contact with the object for producing an electrical output indicative of the level of received light, and analyzer means connected to receive the output of said light sensitive means for producing an electrical output indicative of the difference between the output of said light sensitive means when the object is illuminated via said filter assembly and when the object is in relative darkness due to interruption of the passage of light by one of said vanes.

12. Optical measuring apparatus comprising a soure of wide band light for illuminating an object, a multipler filter assembly having a rotatable axle and a plurality of optical filters fixed to said axle forming therewith a paddlewheel configuration, said assembly being positioned relative to the light path defined said light source and the object such that the filters are swepth through said light path individually during rotation of said axle, light sensitive means operatively positioned to produce an output indicative of the level of light received from said source after passing through one of said filters and coming into optical contact with said object, logic means responsive to the rotation of said axle for producing an plurality of outputs indicative of illumination of said object by certain wavelengths of light, logarithmic amplifier means operatively receiving the output of said light sensitive means, a pair of sample and hold circuits operatively connected to receive the output of said logarithmic amplifier means and connected respectively for selective control by said logic means, differential amplifier means operatively connected to receive the outputs of said pair of sample and hold circuits to produce an output indicative of $\Delta$ OD, wherein $\Delta$ OD represents the difference in optical density at a pair of different wavelengths, a plurality of additional sample and hold circuits operatively connected to receive the output of said differential amplifier and respectively connected for selective control by said logic means to store separate outputs indicative of $\Delta$ OD at different pairs of wavelengths, and computer means operatively receiving the outputs of said additional sample and hold circuits for computing the value of a mathematical function of the outputs of said additional sample and hold circuits.

13. The apparatus of claim 12, further comprising transducer means operatively connected to said axle for providing an output to said logic means indicative of the instantaneous angular position of said filter assembly during rotation.

14. The apparatus of claim 13, further comprising sensor amplifier means connected between said light sensitive means and said logarithmic amplifier means, said filter assembly including means for regularly interrupting the passage of light from said light source to the object to produce dark periods, said logic means producing an output to said sensor amplifier means indicative of said dark periods, said sensor amplifier unit having means responsive to the output of said logic means indicative of said dark periods for producing an output proportional to the difference between the outputs of said light sensitive means when said object is illuminated and when said object is in relative darkness.

15. Optical apparatus, comprising a source of wide band light for illuminating an object, a light path being defined between said source and said object, a plurality of narrow band optical interference filters, mounting means for successively moving individual ones of said filters through said light path to intercept and filter said wide band light and for continuously reorienting each said filter through a range of angles of incidence of said light path relative to said filter as said filter moves through said light path, light passing through each one of said filters being restricted to continuously shifting bandwidths as a function of the instantaneous size of said angle of incidence for a given filter, at least one photosensitive means positioned to receive light from said source after passing through one of said filters and coming into optical contact with said object and to produce a signal representing the amplitude of said reflected light, and means responsive to said signal to provide an indication of the characteristic of said object.

16. The apparatus of claim 15, further comprising indicator means interconnected with said mounting means for providing output signals corresponding respectively to a plurality of predetermined discrete orientations of each said filter in said light path in order to identify the bandwidth of light being passed to the object at any given time.

* * * * *